(12) United States Patent
Hashimshony et al.

(10) Patent No.: US 9,498,192 B2
(45) Date of Patent: Nov. 22, 2016

(54) SURGICAL TOOL

(75) Inventors: Dan Hashimshony, Givat Ada (IL); Gil Cohen, Jerusalem (IL)

(73) Assignee: DUNE MEDICAL DEVICES LTD., Caesarea (IL)

( * ) Notice: Subject to any disclaimer, the term of this patent is extended or adjusted under 35 U.S.C. 154(b) by 0 days.

(21) Appl. No.: 13/387,504

(22) PCT Filed: Aug. 3, 2010

(86) PCT No.: PCT/IL2010/000629
§ 371 (c)(1),
(2), (4) Date: Jan. 27, 2012

(87) PCT Pub. No.: WO2011/016034
PCT Pub. Date: Feb. 10, 2011

(65) Prior Publication Data
US 2012/0123296 A1 May 17, 2012

Related U.S. Application Data

(60) Provisional application No. 61/328,319, filed on Apr. 27, 2010, provisional application No. 61/230,842, filed on Aug. 3, 2009.

(51) Int. Cl.
*A61B 10/02* (2006.01)
*A61B 10/06* (2006.01)

(52) U.S. Cl.
CPC ....... *A61B 10/0266* (2013.01); *A61B 10/0275* (2013.01); *A61B 10/06* (2013.01)

(58) Field of Classification Search
CPC .................. A61B 10/0266; A61B 10/0275
(Continued)

(56) References Cited

U.S. PATENT DOCUMENTS 4,955,383 A 9/1990 Faupel
5,227,730 A 7/1993 King et al.
(Continued)

FOREIGN PATENT DOCUMENTS

CN 1356546 A 7/2002
WO WO 96/12439 5/1996
(Continued)

OTHER PUBLICATIONS

Jul. 25, 2013 European Search Report issued in Application No. EP 10 80 6147.4.
(Continued)

*Primary Examiner* — Linda Dvorak
*Assistant Examiner* — Emily Lloyd
(74) *Attorney, Agent, or Firm* — Browdy and Neimark, P.L.L.C.

(57) ABSTRACT

A surgical tool for use in a tissue removal procedure from a subject is described. The surgical tool has proximal and distal regions and at least one sensor for sensing one or more predetermined conditions located at a distal region of the surgical tool. And a substantially flat signal transmission structure electrically connected with the at least one sensor and extending between the location at the distal region and the proximal region. The signal transmission structure is configured for providing impedance controlled signal transmission between the at least one sensor and the proximal region.

25 Claims, 11 Drawing Sheets

(58) Field of Classification Search
USPC .................................... 600/564, 566, 567
See application file for complete search history.

(56) References Cited

U.S. PATENT DOCUMENTS

| | | | |
|---|---|---|---|
| 5,334,941 | A | 8/1994 | King |
| 5,573,008 | A | 11/1996 | Robinson et al. |
| 5,957,863 | A | 9/1999 | Koblish et al. |
| 6,169,254 | B1 | 1/2001 | Pant et al. |
| 6,380,747 | B1 | 4/2002 | Goldfine et al. |
| 6,402,689 | B1 | 6/2002 | Scarantino et al. |
| 6,411,103 | B1 | 6/2002 | Tobias et al. |
| 6,494,829 | B1 | 12/2002 | New, Jr. et al. |
| 6,546,787 | B1 | 4/2003 | Schiller et al. |
| 6,770,070 | B1 | 8/2004 | Balbierz |
| 6,813,515 | B2 | 11/2004 | Hashimshony |
| 7,087,061 | B2 | 8/2006 | Chernenko et al. |
| 7,171,252 | B1 | 1/2007 | Scarantino et al. |
| 2002/0128570 | A1 | 9/2002 | Bowman et al. |
| 2003/0187366 | A1 | 10/2003 | Hashimshony |
| 2004/0097965 | A1 | 5/2004 | Gardeski et al. |
| 2005/0021019 | A1 | 1/2005 | Hashimshony et al. |
| 2006/0004286 | A1* | 1/2006 | Chang et al. ................. 600/587 |
| 2006/0058676 | A1 | 3/2006 | Yagi et al. |
| 2006/0178699 | A1 | 8/2006 | Surti |
| 2006/0264738 | A1 | 11/2006 | Hashimshony et al. |
| 2007/0016101 | A1 | 1/2007 | Feldman et al. |
| 2007/0208271 | A1 | 9/2007 | Voegele |
| 2008/0021343 | A1 | 1/2008 | Hashimshony et al. |
| 2008/0200803 | A1 | 8/2008 | Kwon et al. |
| 2009/0062637 | A1 | 3/2009 | Hashimshony et al. |
| 2009/0322347 | A1 | 12/2009 | Hashimshony et al. |

FOREIGN PATENT DOCUMENTS

| | | |
|---|---|---|
| WO | WO 2006/085052 A2 | 8/2006 |
| WO | WO 2006/103665 A2 | 10/2006 |
| WO | WO 2007/070093 A2 | 6/2007 |
| WO | WO 2009/010960 A2 | 1/2009 |
| WO | WO 2009/156982 A2 | 12/2009 |

OTHER PUBLICATIONS

Bogosanic, M. and Williamson, A.G., "Microstrip Antenna Array with a Beam Focused in the Near-Field Zone for Application in Noncontact Microwave Industrial Inspection", *IEEE Transactions on Instrumentation and Measurement*, Dec. 2007, pp. 2186-2195, vol. 56, No. 6.

Klemm, M. et al., "Radar-Based Breast Cancer Detection Using a Hemispherical Antenna Array—Experimental Results", *IEEE Transactions on Antennas and Propagation*, Jun. 2009, pp. 1692-1703, vol. 57, No. 6.

Gibbins, D. et al., "Design of a UWB Wide-Slot Antenna and a Hemispherical Array for Breast imaging", *Antennas and Propagation 2009*, May 2009, pp. 2967-2970, EuCAP 2009, $3^{rd}$ European Conference.

* cited by examiner

SURGICAL TOOL

FIELD OF THE INVENTION

This invention is generally in the field of medical devices, and relates to a surgical tool, such as a biopsy tool or the like for tissue removal.

BACKGROUND OF THE INVENTION

Minimally invasive surgical procedures are widely used today instead of major surgery procedures, or as preliminary procedures allowing inspection of diseased/abnormal tissues of the subject (e.g. patient's body). In such procedures, relatively small surgical tools are typically directed through the body portion towards the region of interest therein (for example utilizing natural cavities (lumens) in the body, or minimal surgical openings, e.g. single-aperture or multi-aperture laparoscopy).

It is very often the case that such minimally invasive procedures are incapable of examining the region of interest (e.g. the type of the tissue thereon) in real time just prior to removing the tissue portion. Various techniques have been developed to facilitate tissue inspection while removing the tissue portions, and are described for example in the following publications:

U.S. Pat. No. 4,955,383 discloses a method and apparatus for determining the presence or absence of a disease condition at a test site on a human or animal subject by detecting during a test period the respective electrical potentials of the electromagnetic field present in the subject between each of a plurality of measurement locations in the area of the test site and at least one reference location. A representative potential is separately obtained for each measurement location during the test period, and these representative potentials are compared at the end of the test period to obtain relationships therebetween which are indicative of either the presence or absence of a disease condition. US patent publication No. 2002/128570 discloses technique for quantifying perfusion and removing a biopsy sample at a site in a living body wherein an instrument having a perfusion sensor is introduced into the body at a site to be investigated to there interrogate the tissue. The biopsy specimen is collected when the perfusion sensor produces a signal indicative of perfused, viable tissue.

U.S. Pat. No. 6,546,787 discloses diagnostic imaging methods, methods of detecting the margin of tissue structures and bioresponsive needle systems are disclosed. The methods rely on the use of strain signals provided by a strain gage mounted on the wall of one or more needles as the needle or needles are moved through tissue. The systems employ a strain gage mounted on the wall of the needle and a strain monitor providing feedback to a user.

GENERAL DESCRIPTION

There is a need in the art for facilitating a surgical procedure by providing simple and effective in-situ tissue characterization mechanism, which can be easily incorporated in the known surgical tools, such as biopsy needles.

According to the invention, a novel sensor structure is provided, which is based on impedance controlled signal transmission, and which can be incorporated in a surgical tool of practically any known type. Thus, the present invention provides a novel surgical tool having a tissue removal assembly and carrying a tissue characterization assembly utilizing impedance controlled signal transmission. The tissue characterization assembly is mounted on the surgical tool such that the tissue characterization is applicable just before and without affecting the tissue removal procedure.

In this connection, the following should be understood: Conventional electro-magnetic (EM) tissue characterization devices/sensors, such as near field EM sensors, are in many cases operated by inducing high frequency EM fields in the tissue to be characterized (e.g. high frequency electro magnetic fields in the range of radio-frequency, RF, and microwave, MW, frequency regimes). Accordingly, such conventional EM tissue characterization devices/sensors are typically configured with controlled impedance signal transmission structures, such as coaxial signal transmission cords including an inner conductor signal line surrounded by a flexible, tubular insulating layer which is in turn surrounded by a tubular conducting shield.

However, due to the coaxial structure of such impedance controlled signal transmission cords, such cords generally occupy a significant volume (e.g. relatively to the volume of the inner conductor signal line), and thus accommodating such electro-magnetic tissue characterization sensors within small/narrow surgical tools, such as biopsy tools/needles, is cumbersome, complicated and might be practically impossible without modifying the surgical tool itself.

Moreover, since generally each coaxial signal transmission cord is suited for carrying impedance controlled signal to only one coaxial sensing region, utilizing multiple sensors (i.e. EM tissue characterization sensors) might also be impractical even for relatively large surgical tools. This is because a bundle of coaxial impedance controlled signal cords (one per each sensor) is required to pass along the surgical tool.

EM tissue characterization sensors, such as near field EM sensors, typically have a coaxial aperture (i.e. concentric sensing aperture defining a sensing surface). In the conventional approach for impedance controlled signal transmission, a coaxial signal transmission cord has to be oriented perpendicularly to the sensing surface/plane of the sensor. As a result, in the configurations where sensor(s) should be accommodated on the side facet(s) of an elongated surgical tool, bending of the coaxial signal transmission cord is required to allow it to approach the side facet of the surgical tool in the perpendicular direction. In turn, additional space will be required in the surgical tool for accommodation of the bending radius of the cord, making such configurations further inapplicable for narrow surgical tools.

Furthermore, some surgical tools, such as biopsy needles, are constructed with an enclosure defining a hollow cavity that has certain functional purposes in the tool operation (such as collection and accommodation of tissue sample(s) therein). In such surgical tools, an impedance controlled signal transmission structure should extend along the facets of the enclosure (from the interior or exterior of the surgical tool) in a manner that does not impede the proper operation of the surgical tool. Hence, the use of coaxial cords having a relatively large cross-sectional dimension (e.g. of the order of the required cross sectional dimensions of the surgical tool) might be also impractical.

Also, some surgical tools have moving parts shiftable/movable with respect to one another. Transferring an impedance controlled coaxial signal transmission structure of the conventional type (e.g. coaxial cords) to extend along and between movable parts of such surgical tools, is difficult to implement as the bending radius of such coaxial cord would be relatively large, as well as might require application of substantial force for bending.

The above problems are solved in the present invention by utilizing EM tissue characterization sensor(s) having a substantially flat impedance controlled signal transmission structure (such as planar feed structures) integrated therewith. Impedance controlled planar feed structures, such as strip- and microstrip-structures are integrated with one or more electromagnetic tissue characterization sensors thereby allowing impedance controlled signal transmission to be provided to and from the sensors by utilizing flat structures having relatively small volume.

Signal transmission structure(s) together with the tissue characterization sensor(s) integrated therewith (referred to collectively herein as a tissue characterization assembly) may be fabricated for example utilizing the so-called flexible or rigid-flexible circuit techniques or combination thereof. Fabrication of such tissue characterization assembly can be implemented directly on (integral with) one or more surfaces (or facets) of the surgical tool (e.g. such that the signal transmission structures are attached and/or integrated with the surface of the tool). Generally, the fabrication of the tissue characterization assembly can be carried out independently from or in-situ with the surgical tool, e.g. the assembly is fitted/attached/bonded to the surgical tool.

Hence, according to the invention, the tissue characterization assembly (the signal transmission structure and EM tissue characterization sensor(s) integrated therewith) is configured with a substantially flat form factor (e.g. their length and width characteristic length scales are substantially larger than their thickness). This allows placing the impedance controlled signal transmission structure(s) along and/or within various types of small/narrow surgical tools without a need for enlarging the tool's dimensions or for interrupting its proper functionality. The flat EM tissue characterization sensors formed according to the technique of the present invention may be accommodated on the external and/or internal facets of the surgical tools.

Surgical tools according to the present invention may be any surgical tools for example tissue removal and collection tools, such as biopsy tools, as well as other surgical tools, such as tissue ablation tools. More specifically, the present invention is used with biopsy tools (e.g. needles) of the kind defining a hollow cavity having specific functions in the tool operation, and is therefore described below with respect to this specific application. It should, however, be noted that the invention is not limited to this specific example. Considering the cavity-containing elongated surgical tool, the flat impedance controlled signal transmission structure can extend along the facet(s) of the surgical tool (or of the enclosure thereof) in a manner that it does not disturb the proper operation of the surgical tool. In this connection, it should be understood that for the purposes of the present application, the expression "elongated tool" refers to a structure that has a distal region involved in the tissue inspection/removal procedure (e.g. by which the tool is brought to a tissue to be examined) and has a proximal region which is typically kept aside from said tissue, and needs not be limited by any geometry/shape of such structure. Typically however, such tools have elongated geometry (slender), and the invention can advantageously be used in such tools.

The integration of the EM tissue characterization sensor(s) with the signal transmission structure(s) is implemented, according to the invention, in a co-planar configuration in which there is at least one continuous surface common to the sensor(s) and the signal transmission structure(s). Accordingly, the signal transmission structure may be connected with the sensors in parallel to the sensing surface of the sensors, which allows placing the entire tissue characterization assembly so as to extend along and adjacent to one or more facets of the surgical tool without occupying substantial volume thereon, occupying a volume that neither affects the regular operation of the tool nor needs any modification of the existing tool.

This configuration is advantageous over other impedance controlled signal transmission utilizing the coaxial signal transmission cord (or cable), because the use of a flat signal transmission structure, such as microstrip or strip-planar feed structures, thus enabling accommodating impedance controlled signals while occupying a minimal volume within the surgical tool. Also, the flat signal transmission structure may be formed as a flexible structure that enables bending (e.g. static bending) of the structure along and/or adjacent to curved facets of the surgical tool, and also enables bending (dynamic bending) of the signal transmission structure together with the flexible elements of the surgical tool, or bending in regions in which the signal transmission structure extends between movable parts of the tool. Moreover, in such flat impedance controlled signals transmission structures, multiple signal lines can be included in the single structure for multiple sensors, thus enabling to further reduce the volume for accommodation of multiple signal transmission lines.

Thus, according to a broad aspect of the present invention there is provided a surgical tool for use in a tissue removal procedure from a subject. The surgical tool has proximal and distal regions and includes at least one sensor located at the distal region and adapted for sensing, during operation of the surgical tool, one or more predetermined conditions of a tissue in the vicinity of the a distal region of the surgical tool. The surgical tool includes a substantially flat signal transmission structure electrically connected with said at least one sensor and extending between the location of the sensor at the distal region and the proximal region. The signal transmission structure being configured for providing impedance controlled signal transmission between said at least one sensor and said proximal region.

According to some embodiments of the invention the surgical tool is configured as a biopsy tool (e.g. a biopsy needle) and may include a cavity for collection of a removed tissue therein.

According some embodiments of the invention the signal transmission structure includes an electrically conductive layer and at least one signal connection line associated with at least one sensor. Preferably the signal transmission structure is integral with at least one sensor located on the distal region of the surgical tool (e.g. having at least one common continuous surface therewith).

At least one sensor, located at the distal region of the surgical tool, may be configured and operable as a tissue characterization sensor (e.g. including a coaxial sensing aperture). Preferable the sensor is a near field electromagnetic sensor comprising the coaxial sensing aperture surrounded by an electrically conductive material, such that when the tool is in operation the sensor faces a tissue portion by said coaxial sensing aperture. Such a near field electromagnetic sensor may include for example an inner conductor element coupled to inside of said coaxial sensing aperture and electrically coupled to a signal connection line of the signal transmission structure.

The surgical tool of the present invention may include a resistive type near field electromagnetic sensor(s), the inner conductor element thereof being electrically insulated from the surrounding electrically conductive material. Resistive type sensor(s) may include an electrical insulator material covering the sensing region of the sensor for insulating near field electromagnetic sensor from a tissue. Alternatively such resistive type sensor may be configured to perform measurement while the inner conductor element and the surrounding electrically conductive material are brought in direct contact with a tissue. Alternatively or additionally surgical tool of the present invention may include inductive type near field electromagnetic sensor(s). In this type of sensors the inner conductor element is electrically connected to the electrically conductive material surrounding the coaxial sensing aperture.

According to some embodiments of the invention, the signal transmission structure includes flexible structure configured and operable for impedance controlled signal transmission therethrough. In some cases the flexibility of the signal transmission structure allows traversing the signal transmission structure alone the surgical tool while bending the signal transmission structure in proximity to curved facet thereof. Alternatively or additionally, according to some embodiments of the invention the surgical tool has an extendable part which is shiftable between its retracted and extracted positions with respect to its proximal region flexible structure being electrically connected to at least one sensor accommodated on said extendable part and allowing extraction and retraction of said extendible part in between said positions.

It should be understood that the surgical tool of the invention may include a plurality of at least two sensors, at least one of said plurality of sensors being said sensor located on the distal region of said surgical tool. The multiple sensors are arranged in a spaced apart relationship along a direction between said proximal and distal regions.

BRIEF DESCRIPTION OF THE DRAWINGS

In order to understand the invention and to see how it may be carried out in practice, embodiments of the invention will now be described, by way of non-limiting examples only, with reference to the accompanying drawings, in which:

FIGS. 2A and 2B are schematic illustrations of two types of biopsy needles according to the present invention; FIGS. 2C and 2D exemplify surgical tool for multiple biopsy sampling; FIG. 2E shows an example of a surgical tool for sampling, removal and collection of tissue including a catheter and a gripping mechanism; FIG. 2F is an illustration of a surgical tool associated with a deflectable biopsy ablation catheter including two jaws for sampling and ablating tissue; FIGS. 2G and 2H are schematic illustrations of top and cross sectional views of a surgical tool including tissue characterization sensors located within a tissue collection cavity of the surgical tool; FIG. 2I illustrates another example of surgical tool including a vacuum communication channel and one or more vacuum ports located in the vicinity of tissue characterization sensors; FIG. 2J exemplifies a surgical tool comprising a deflectable biopsy forceps catheter;

FIG. 4A shows a strip planar structure; FIG. 4B shows a micro strip planar structure and; FIG. 4C show a micro strip planar structure with multiple signal transmission lines;

FIGS. 5A to 5D exemplify sensors having a hexagonal geometry of the sensing region contour, FIGS. 5E and 5F exemplify sensor cells having a rectangular geometry of the sensing regions; FIGS. 5A to 5C exemplify sensors having inner conductor elements of a circular cross-section, and FIGS. 5D to 5F show sensors having various other geometries of the cross-section at the distal end of the inner conductor elements; FIGS. 5A to 5C and 5F show resistive type sensors in which the inner conductor element is electrically insulated from the contour of the respective sensing region and FIGS. 5D and 5E show inductive type sensors having their inner conductor element electrically connected to the contours of the respective sensing regions;

DETAILED DESCRIPTION OF EXEMPLARY EMBODIMENTS

Figure 1:
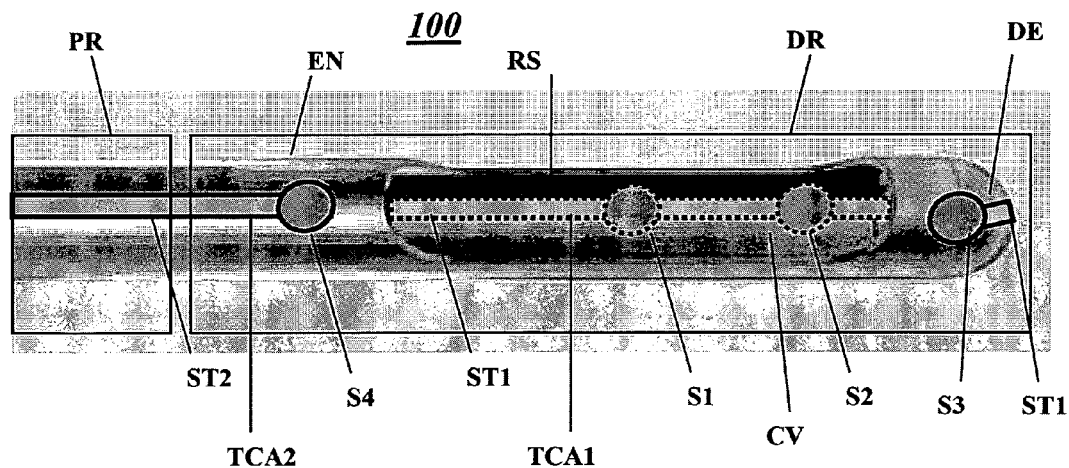
FIG. 1 shows a schematic illustration of a surgical tool according to an embodiment including tissue characterization assembly.

Reference is made to FIG. 1 illustrating schematically a surgical tool 100 according to an embodiment of the present invention configured an operable for tissue removal and collection procedure/operation. The surgical tool has proximal and distal regions, PR and DR, respectively, and defines a cavity CV for collection of a removed tissue sample. The surgical tool 100 includes a tissue removal assembly and a tissue characterization assembly. The latter includes at least one sensor (four sensors in the present example S1, S2, S3 and S4) arranged at the distal region DR of the surgical tool 100 and connected to at least one impedance controlled signal transmission structure of the surgical tool 100 extending in between the proximal region PR and the distal region DR and further within the distal region DR towards the locations of the sensors thereon. Accordingly, impedance controlled signal transmission structure provides controlled impedance signal transmission in between the proximal region PR and the sensors. Two impedance controlled signal transmission structures, ST1 and ST2, are illustrated in the present example connected respectively to sensing regions of respectively sensors S1, S2, S3 and sensor S4.

Actually, the signal transmission structure ST1 together with the sensors S1, S2 and S3 electrically connected thereto and the signal transmission structure ST2 together with its associated sensor S4, define two tissue characterization assemblies TCA1 and TCA2. It should be understood that generally the surgical tool 100 according to the invention may include one or more such tissue characterization assemblies.

The surgical tool 100 exemplified in the present embodiment is a biopsy needle. The distal region DR of the surgical tool 100 is adapted for being inserted/penetrated into a subject/tissue-mass to be inspected (in-vivo or in-vitro), and to enable removal and collection of tissue portion(s)/sample(s) therefrom. The tissue sample(s) removed from the inspected tissue-mass are collected in the cavity CV of the surgical tool 100. The proximal region PR of the surgical tool 100 may be functioning as a handle of the surgical tool 100 and typically remains outside the inspected subject/tissue-mass during a tissue removal and collection procedure/operation. The cavity CV, in which the tissue pieces are collected, is defined in at least a portion of the distal region DR and may also extend to the proximal region PR of the surgical tool 100 for example in order to enable collection of multiple tissue samples in the cavity CV.

The sensors S1, S2, S3 and S4, which are arranged at the distal region DR of the surgical tool 100, have sensing regions/surfaces facing towards the exterior of the surgical tool 100, such that during an operation (e.g. tissue collection procedure) with the surgical tool, when the distal region DR is inserted in to the tissue mass, the sensing regions of at least some of the sensors S1, S2, S3 and S4 are exposed to the tissue-mass.

In this respect, it should be noted that sensors S1 and S2, illustrated with dashed lines, are located at outer surface on the back side of the surgical tool 100.

It should be also understood that although in the present embodiment four sensors and two impedance controlled signal transmission structures are illustrated being part of two tissue characterization assemblies TCA1 and TCA2, a different number of sensors and/or impedance controlled signal transmission structures can be implemented and arranged, according to the invention, in one or more tissue characterization assemblies incorporated in the surgical tool 100. For example, only one sensor and a single signal transmission structure can be used. Also, the number of sensors connected with each signal transmission structures may vary from one sensor and up to an array of hundreds of sensors and more. In case that more than one sensor is connected to one signal transmission structure, that signal transmission structure typically includes multiple signal connection lines each connected to a different sensor. It should be also noted that when multiple sensors are accommodated on the surgical tool, the sensors may be of the same or different types. Multiple sensor types allow examining different properties/conditions of the tissue in the vicinity of the surgical tool, while multiplicity of sensors of the same type allow spatial mapping of certain parameters/conditions of the tissue.

Preferably, the impedance controlled signal transmission structures ST1 and ST2 of the surgical tool 100 are substantially flat structures which can thus be accommodated within small sized and/or narrow parts of the surgical tool (such as on a needle part of the tool). In the present example, the tissue characterization assemblies TCA1 and TCA2 are formed as integrated structures/circuits in which sensors S1, S2 and S3 are integrated with the signal transmission structure ST1 and the sensor S4 is integrated with the signal transmission structures ST2.

The signal transmission structures, ST1 and ST2, extend between the sensors at the distal region DR of the surgical tool 100, and the proximal region PR of the tool, and are configured and operable for providing impedance controlled signal transmission between the sensors and said proximal region. In the present example, signal transmission structure ST2 is electrically connected only to the sensor S4 located at the front side of the surgical tool 100. Signal transmission structure ST1, which is electrically connected to three sensors S1, S2 and S3, extends along the backside of the surgical tool, at which it is connected to sensors S1 and S2, and upstream therefrom it is bend/wrapped about the closed distal end DE of the surgical tool and is electrically connected to the sensor S3 located thereon, on the tip of the surgical tool 100.

Utilizing one or more sensors on the distal region of the surgical tool allows determining different conditions of the tissue surrounding the surgical tool and/or providing more precise measurement/distribution of the same parameter value. Also, during insertion/movement of the surgical tool within the tissue-mass, scanning of the different tissue(s) (tissue types) through which the surgical tool penetrates can be provided utilizing the information (e.g. signals) from the sensor(s). As indicated above, an arrangement of multiple sensors of different types of sensors enables to utilize the data/signals to characterize a wide range of predetermined parameters/conditions of a tissue located in the vicinity of the distal region DR of the surgical tool 100. Alternatively or additionally, utilizing more than one sensor of the same type enables to spatially map properties of a medium or tissue facing/surrounding the distal region DR even when the surgical tool 100 is not moved with respect to the tissue mass. The spatial coverage and resolution of tissue characterization by the sensors is determined according to the number and size of the sensors on the surgical tool 100. Also, the size of the sensing regions/surfaces of the each of the sensors determines the feature detection size each sensor is characterizing as each sensor integrates over the value of the properties of the tissue/medium coupled with its sensing region.

As indicated above, a sensor type suitable for use in the present invention is impedance controlled sensing; this may include inter alia radio frequency (RF) and/or micro wave (MW) sensors, as well as one or more of other electric and magnetic sensors. More particularly, in the present example, sensors S1, S2, S3 and S4 are configured and operable as near-field EM sensors which operate by inducing, within the tissue regions located proximate to the sensor's sensing surface, near EM fields corresponding to signals transmitted to this tissue region from a signal generator. The configuration and strength of the induced fields, per specific sensor type, depends on the dielectric properties of the tissue regions adjacent/in close proximity to the sensor's sensing surface.

Accordingly, during surgical procedure with the surgical tool (e.g. tissue collection procedure by the biopsy needle), the sensors S1, S2, S3 and S4 are capable of sensing one or more predetermined conditions of the tissue-mass located at the vicinity of the distal region DR. In embodiments of the invention where the sensors S1, S2, S3 and S4 are near field electromagnetic sensors, a radio frequency (RF) signal is transmitted to and from the sensors S1, S2, S3 and S4 through the respective impedance controlled signal transmission structures ST1 and ST2 connected thereto. Tissue characterization is obtained by analyzing the signals transmitted through signal transmission structures ST1 and ST2 to determine one or more predetermined conditions of the tissue which correspond to the impedance of portions of the tissue in the vicinity of the sensing regions of the sensors S1, S2, S3 and S4. Thus, the signal transmission structures ST1 and ST2 provide impedance controlled signal transmission therethrough.

In the present non limiting example, the surgical tool 100 is constructed as a hollow elongated enclosure EN defining the cavity CV thereinside and having a tube like shape closed at its distal end DE. The cavity CV has a recess RS made at the distal region DR of the surgical tool 100 for collecting tissue being removed.

The surgical tool 100 includes multiple sensors (S1-S4) electrically connected and integrated with flat signal transmissions structures ST1 and ST2 such as strip or micro-strip structures. This types of signal transmission structure can be configured as substantially flat (thin) structures (e.g. their length and width characteristic length scales being substantially larger than their thickness) which allow transferring the impedance controlled signal transmission structure(s) along the enclosure of the surgical tool without interrupting the functionality of tissue collection by the cavity CV. Such flat impedance controlled signal transmission structure(s) ST1 and ST2 configured as strip and/or micro-strip signal transmission structures will be described below with reference to FIGS. 4A-4C. Such flat signal transmission structures can be transferred along and adjacent to one or more facets of the surgical tool 100 such as not to interrupt the operation of the surgical tool and not to occupy substantial volume. The flat signal transmission structure(s) can, for example be, attached/bonded to the walls/facets of the surgical tool 100 by suitable paste/glue and/or it can for example be located/bounded within depression(s) in one or more facets of the surgical tool 100. Alternatively or additionally at least part of the signal transmission structure may be integrated with one or more surfaces of the surgical tool, for example such surfaces may serve as a ground plane/ surface of the signal transmission structure as described further below.

Preferably, the flat impedance controlled signal transmission structures ST1 and ST2 are flexible structures allowing transfer of the signal transmission structures ST1 and ST2 along curved paths (e.g. curved surfaces of the surgical tool 100) and also enabling dynamic bending of the structures engaging with movable parts of the surgical tool. For example in the present example, signal transmission structure ST1 is bend (along its longitudinal direction) over the tip (over the distal end DE) of the surgical tool 100 such that sensor S3 can be accommodated near the distal end DE. Moreover, as the surgical tool 100 in the present example has a cylindrical shape, signal transmissions structures ST1 and ST2 are bend across their width directions at the regions at which they extend attached to the side walls of the surgical tool 100.

It should be noted that in the present example, the sensors S1-S4 are physically coupled to their respective signal transmission structures ST1 and ST2 in a co-planar coupling. Actually, differently from coaxial signal transmission structures, according to the present invention the signal transmission structures are coupled in parallel to the sensing region/surface of the sensor and not in perpendicular thereto as in the typical coaxial signal transmission cords.

The sensors (at least one sensor, e.g. sensor S4 in the above-described example) and the signal transmission structure(s) associated therewith, e.g. ST2, are formed together in an integral structure configuration in which the sensor and the signal transmission structure have at least one common continuous surface. The configuration and operation of the signal transmission structure together with a near field tissue characterization sensor will be described below with reference to FIGS. 3A-3C.

As indicated above, incorporation of a flexible signal transmission structure within a surgical tool is advantageous also because it enables to locate sensor on movable and/or retractable parts of the surgical tool. Various examples of the configuration of surgical tools, particularly surgical tools for tissue removal and collection, suitable for utilizing the invention will now be described. In these examples, the tissue characterization sensor(s) are mounted on a biopsy tool (e.g. biopsy needle), for example using one or more sensors located on shiftable/retractable parts of the surgical tool.

Figure 2A:
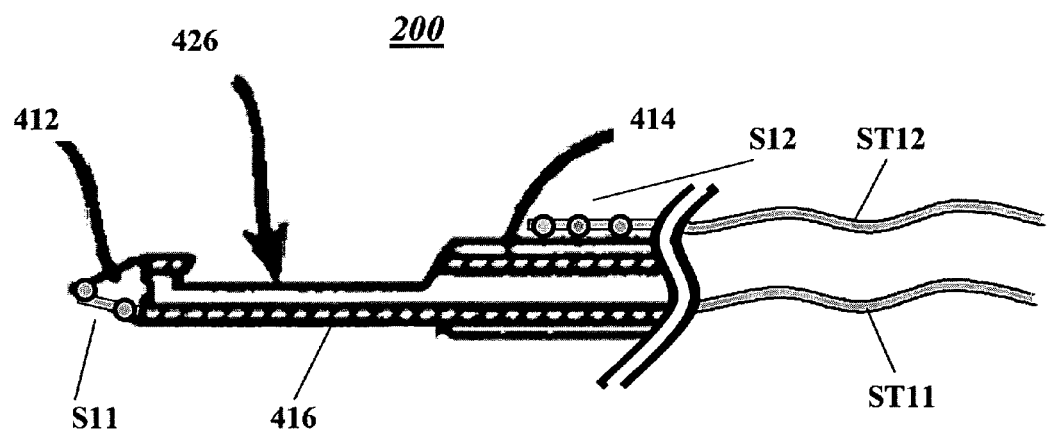
FIGS. 2A to 2J exemplify various surgical tools incorporating a tissue characterization assembly according to the present invention.

Reference is made to FIG. 2A illustrating an embodiment of a surgical tool according to the present invention configured as a biopsy needle 200A incorporating a tissue characterization sensing assembly. In this example a rigid type needle of the conventional configuration is used, for example similar to that described in US patent publication No. 2007/208271. The biopsy needle 200 includes an outer cannula 414 and an inner cannula 416 threaded within the outer cannula 414 and including a closed, distal tissue penetrating tip 412 adapted for piercing tissue and a side tissue sample port 426 disposed proximally of the tip 412. The biopsy needle 200 includes a pair S11 of tissue characterization sensors located on the distal tissue penetrating tip 412 of the inner cannula and a triplet S12 of tissue characterization sensors located on the outers surfaces of the outer cannula 414 at its distal end. The triplet of sensors S12 is electrically connected to a flat signal transmission structure ST12 which is extending along the outer surface of the outer canola 414 towards its proximal region and configured for providing impedance controlled signal transmission in between the sensors and the proximal region. Similarly, the pair S11 of tissue characterization sensors is also associated with a separate flat signal transmission structure ST11 extending along outer surface of the inner cannula 416 towards its proximal region. Here, in cases where the proximal end of the inner cannula 416 is terminated within the hollow cavity of the outer cannula, the signal transmission structure ST11 may extend within the cavity of the outer cannula 414 towards its proximal end for providing signal transmission thereto. Accordingly, the extension of the signal transmission structure ST11 within the outer cannula 414 may be configured in such cases with sufficient length and flexibility to allow retracting and contacting of the inner cannula 16 with respect to the position of the outer cannula 414.

Figure 2B:
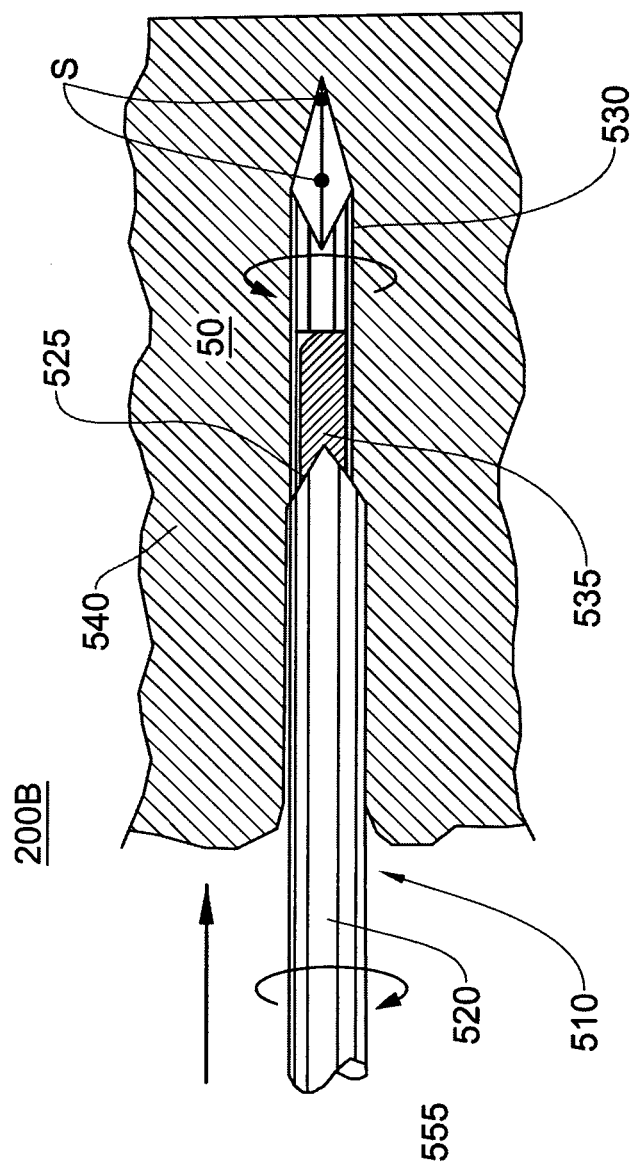

FIG. 2B illustrates a biopsy needle 200B of another type, similar to that described for example in US 2007/0016101. Here, the tissue removal (cutting) is implemented by rotating a stylet 530 about its axis thereby urging a tissue specimen at the biopsy site into a recess 535. A cannula 520, carrying the needle 530, is displaced axially outwardly relative to its retracted position and rotated about its axis in a direction opposite to the direction of rotation of the stylet 530. During the movement of the cannula 520, a cutting edge 525 at the distal end thereof severs the tissue at the biopsy site into the recess 535 of stylet 530. In passing axially and radially across the recess 535, the cannula 520 radially captures a larger biopsy specimen therein. One or more sensors S are mounted on the stylet 530, such that the sensing region is exposed to the tissue adjacent to the stylet while the flexible signal transmission structure (not shown) passes along the outer surface of the stylet without impeding a general procedure of the tissue removal and collection.

Figure 2C:
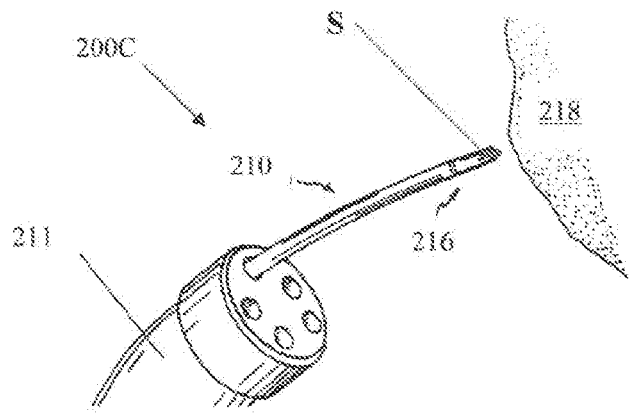
Figure 2D:
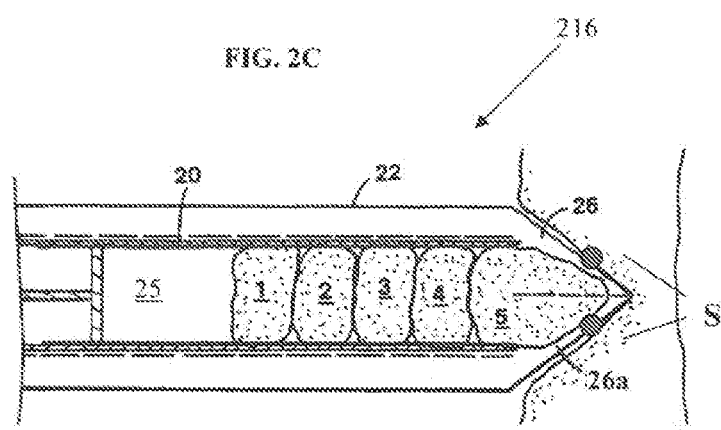

FIGS. 2C and 2D exemplify how the present invention can be incorporated in a surgical tool 200C configured for multiple biopsy sampling. Such surgical tool is described for example in U.S. Pat. No. 5,573,008. The surgical tool may be associated with an endoscope device 211 (e.g., gastroscope, sigmoidoscope, or colonoscope) being introduced into the body via the endoscope channel. In this case, biopsy tools, one such tool 210 being shown in the figure, may be configured as a flexible structure, with a distal sampling portion 216 being extendable from the endoscope 211 for cutting and storing a sample of tissue from a body surface 218 of a patient (e.g. from a surface in the gastrointestinal tract or bronchial tract). For example, the biopsy tool can be configured with a lumen (e.g. flexible) so that it can be advanced over a guidewire, e.g., in vascular applications. The sampling portion 216 carries one or more tissue characterization sensors, generally at S. As shown in FIG. 2D, the portion 216 may include an inner member 20 for storage of multiple, successively taken biopsy samples 1, 2, . . . , 5 in its inner space 25, and an outer cutting member 22. With this configuration, similar of the above described examples, the flexible signal transmission structure, connecting the sensing elements S to the proximal part of the tool outside the body, extends along the surface of the biopsy tool 210 allowing the conventional procedure of the tissue removal and storage.

Figure 2E:
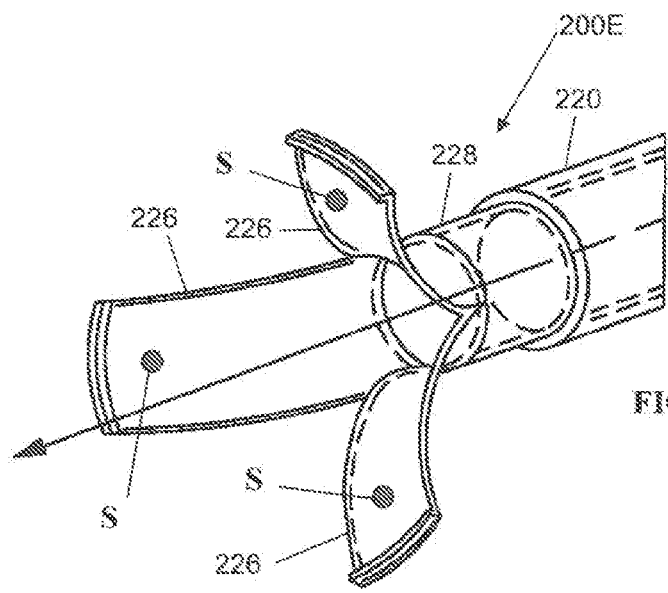

FIG. 2E shows yet another example of a surgical tool 200E for tissue samples removal and collection for further medical analysis. The surgical tool 200E includes a catheter 220 equipped with a gripping mechanism formed by a gripper members 226 mounted on and extendable from a shaft 228. Such a mechanism is described for example in US Patent Publication No. 2006/0178699. The gripping members are configured as or equipped with cutting elements, e.g. along their edges. The gripping members 226 in an open configuration of the gripper mechanism are biased outwardly relative to the longitudinal axis of the shaft 228, and are shiftable into the closed gripping position in which they capture the removed tissue. The gripping members are flexible for movement between their open and closed positions. Tissue characterization sensors S are appropriately mounted on the tool 200E such that sensing regions are located on inner sides of the gripping members and are thus exposed to the tissue in the vicinity of the tool when in the open position of the dripping mechanism, while the flexible signal transmission structure (not shown) extends along the inner surface of the gripping members and further along the shaft thereinside.

Figure 2F:
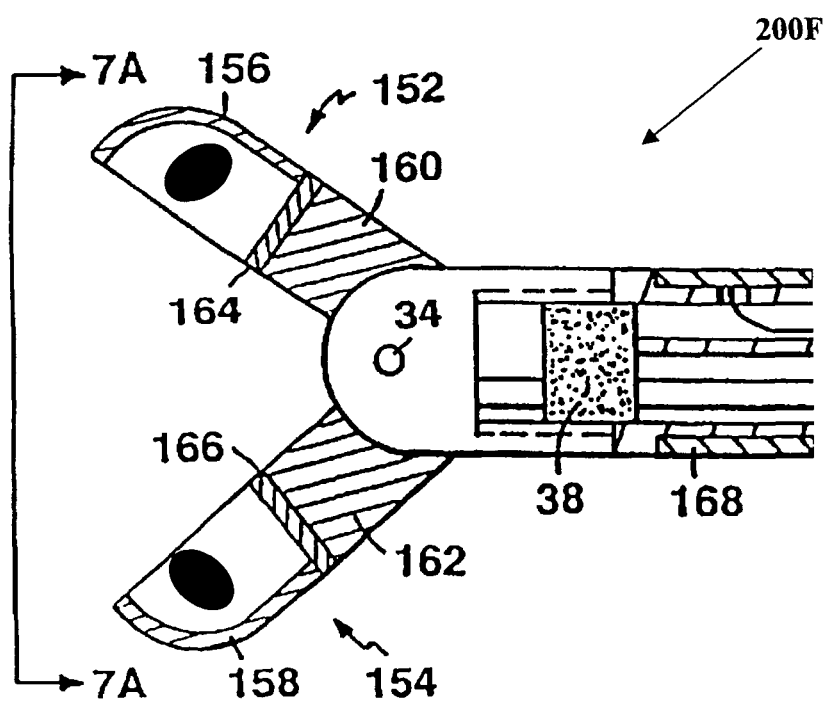

FIG. 2F exemplifies a surgical tool 200F associated with a deflectable biopsy ablation catheter, as described in U.S. Pat. No. 5,957,863. The surgical tool (biopsy catheter) 200F includes two jaws 152 and 154 for sampling a tissue portion and for ablating abnormal tissue. The jaws are shiftable between their open and closed positions (the open position being shown in the figure). When closed, the two jaws form a cavity (by their hollow sections 156 and 158), and when open, expose an electrode surface of ablation electrode sections 160 and 162 to the tissue in the vicinity of the tool allowing said ablation to be implemented. Sensors S are provided on the tool being mounted such that sensing regions are located on inner sides of the jaws and can thus characterize the tissue when the jaws are in their open positions, and the flexible signal transmission structure extends along the tool towards its proximal end, engaging either inner or outer surface of the tool.

Figure 2G:
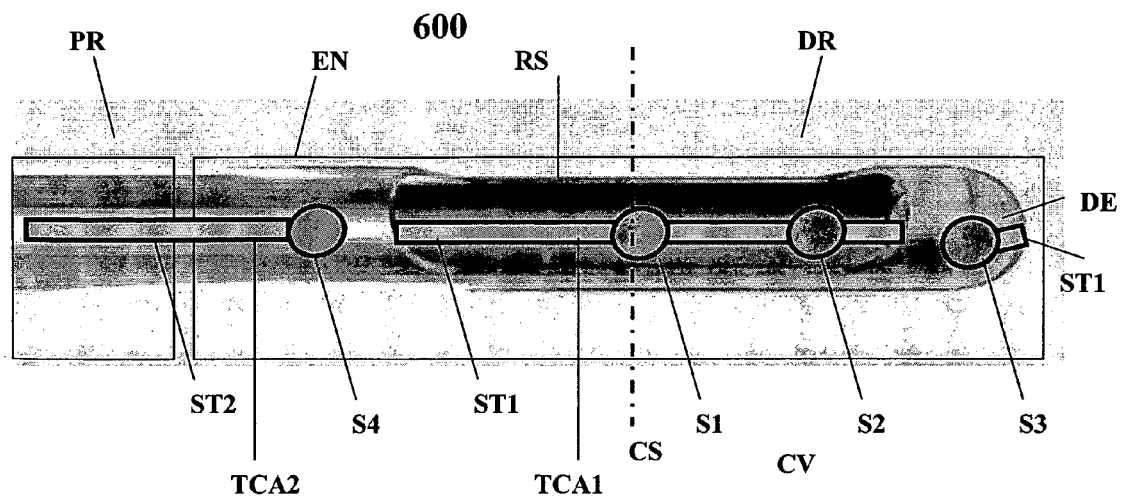
Figure 2H:
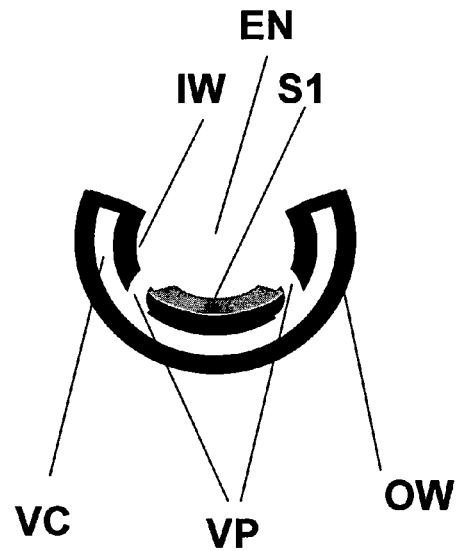

FIGS. 2G and 2H illustrate respectively a top view and cross sectional view of another embodiment of a surgical tool 600 according to an embodiment of the present invention. FIG. 2H is a cross sectional view of the surgical tool 600 taken along the cross section line CS shown in FIG. 2G. Surgical tool 600 is configured for tissue removal and collection similarly to the surgical tool 100 of FIG. 1. Common elements illustrated in surgical tool 100 and in the surgical tool 600 of the present example are designated with the same reference numerals.

In the present example, the sensors S1 and S2 are located on an inner surface of the cavity CV facing the opening of the cavity defined by the recess RS. Accordingly, during tissue collection operation by the surgical tool 600, sensing regions/surface of the sensors S1 and S2 are exposed to tissue portions within the cavity CV.

Also optionally, the surgical tool 600 includes vacuum communication channel. In the present example, the enclosure EN, or parts thereof, include double wall structure including an inner IW and outer OW walls of the enclosure defining the vacuum communication channel VC therebetween. The inner wall 1W of the enclosure is interposed between the cavity CV and the vacuum communication channel VC, and includes vacuum ports/openings VP open towards the cavity CV in the vicinity of the sensors S1 and S2. In operation, vacuum is applied to ports VP through the vacuum channel VC enabling engaging/attaching/coupling of tissue located in the vicinity of the recess RS towards the sensing regions/surfaces of the sensors S1 and S2.

It should be understood that vacuum within the vacuum communication channel VP, can be selectively utilized to cause coupling and decoupling of the tissue to the sensors. It should be also noted that the vacuum state within the vacuum communication channel VC can be controlled independently or in cases where the cavity CV can also be maintained with vacuum conditions, the vacuum state within the vacuum communication channel VC may also be associated with a vacuum state within the cavity CV. Also, the vacuum channel VC can also be used to apply over pressure through the vacuum ports VP for example in order to detach/decouple tissue portions from the vicinity of the sensors S1 and S2. It should be understood that alternatively or additionally other sensors of the surgical tool 600, such as sensor S4, can also be associated with vacuum ports in their vicinity e.g. on the exterior surface of the surgical tool.

Figure 2I:
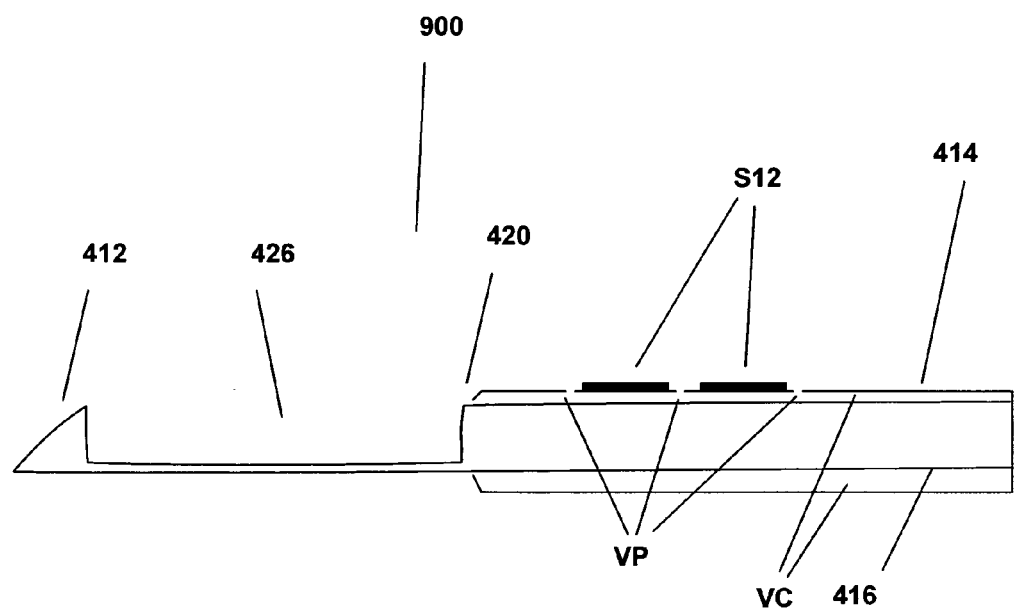

FIG. 2I illustrates a surgical tool 900 configured for tissue removal and collection similarly to the surgical tool of FIG. 2A. Common elements illustrated in surgical tool of FIG. 2A and in the surgical tool 900 of the present example are designated with the same reference numerals.

The surgical tool 900 includes vacuum communication channel VC. In the present example, the outer cannula 414, or parts thereof, is spaced apart from inner cannula 416 defining the vacuum communication channel VC therebetween. The outer cannula 414 includes vacuum ports/openings VP open towards the outer surface of cannula 414 in the vicinity of the sensors S12. In operation, vacuum is applied to ports VP through the vacuum channel VC enabling engaging/attaching/coupling of tissue located in the vicinity of the distal end of cannula 414 towards the sensing regions/surfaces of the sensors S12. Additionally, and optionally, the cannula 414 includes, at its distal end, a resilient member 420 configured fore enhancing the vacuum communication to vacuum ports/openings VP.

Figure 2J:
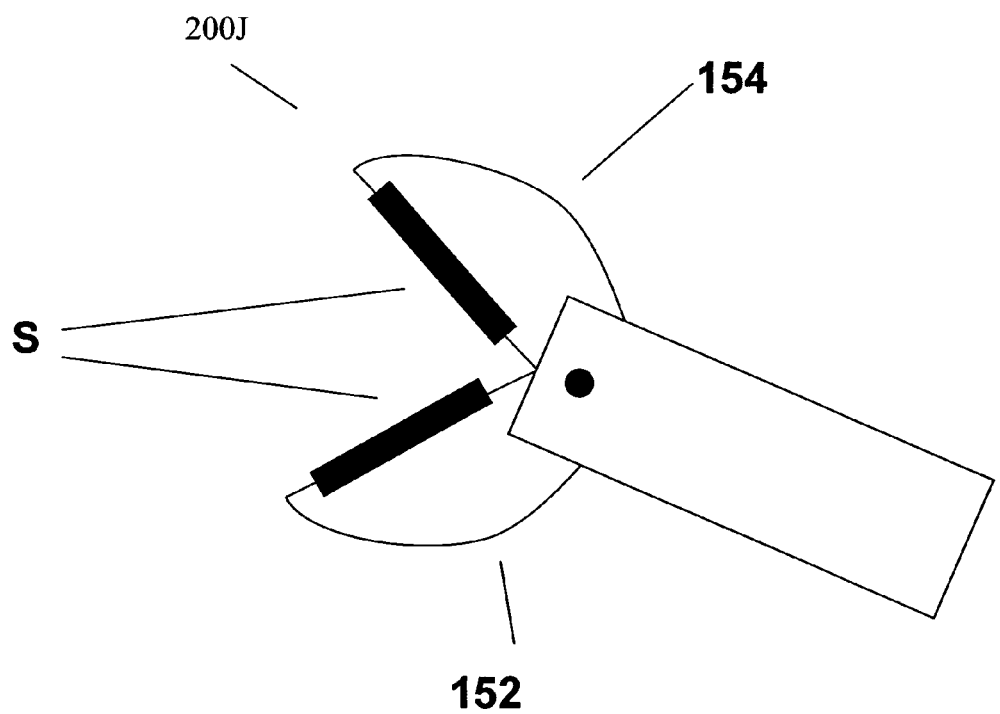

FIG. 2J exemplifies a surgical tool 200J associated with a deflectable biopsy forceps catheter. The surgical tool (biopsy catheter) 200J includes two jaws 152 and 154 for sampling a tissue portion. The jaws are shiftable between their open and closed positions (the open position being shown in the figure). Sensors S are provided on the tool and are mounted such that the sensing regions thereof are located on inner sides of the jaws thus allowing characterization of the tissue when the jaws are in their open positions. The flexible signal transmission structure (not shown) extends along the surgical tool 200J towards its proximal end, engaging either an inner or outer surface of the tool.

It should generally be understood that the surgical tools described above in the different embodiments of the present invention may be used in minimally invasive procedures such as laparoscopic procedure. Such surgical tool may also be used in robotic assisted procedures and/or they may be also employed for examination in non invasive procedures.

The flexibility of the signal transmission structure allows for proper incorporation of the sensor device of the invention with practically any known tissue removal surgical tool. As described above, the tool may be of the kind extendable along an axis of its propagation though the body portion (longitudinal axis of the tool), and/or along axis/axes inclined thereto, e.g. being mounted such that the sensing regions are located on the extendable parts of the tool.

The tissue characterization sensors, as well as the signal transmission structures, are preferably fabricated by the so-called flexible or rigid-flexible circuit techniques. These techniques are used in the present invention for providing flat and flexible/elastic construction of impedance controlled signal transmission structure and also co-planar coupling (and/or integration) of the tissue characterization sensors with the signal transmission structure. As noted above, the flat and co-planar configuration of the signal transmission structure and the sensors allows to locating the sensors and the signal transmission structures thereof along planar/or curved surfaces/facets of surgical tools having narrow or hollow construction. Since the flat and flexible impedance controlled signal transmission structure occupying small volume relatively to other impedance controlled signal transmission structures, such structures can be incorporated on small surgical tools without enlarging the dimensions of the surgical tool.

Also flexibility of such signal transmission structures allows for wrapping the signal transmission structure on curved surfaces of the surgical tool with a small bending radius and/or to transfer the signal transmission structure at regions of the surgical tool at which repetitive movements, such as bending or extraction-retraction of one or more parts of the surgical tool occurs. It should be noted that the technique of the present invention while utilizing the flexibility of the transmission structure of surgical tool still enables passage therethrough of one or more high frequency signal transmission lines to the sensors of the surgical tool.

Figures 3A, 3B:
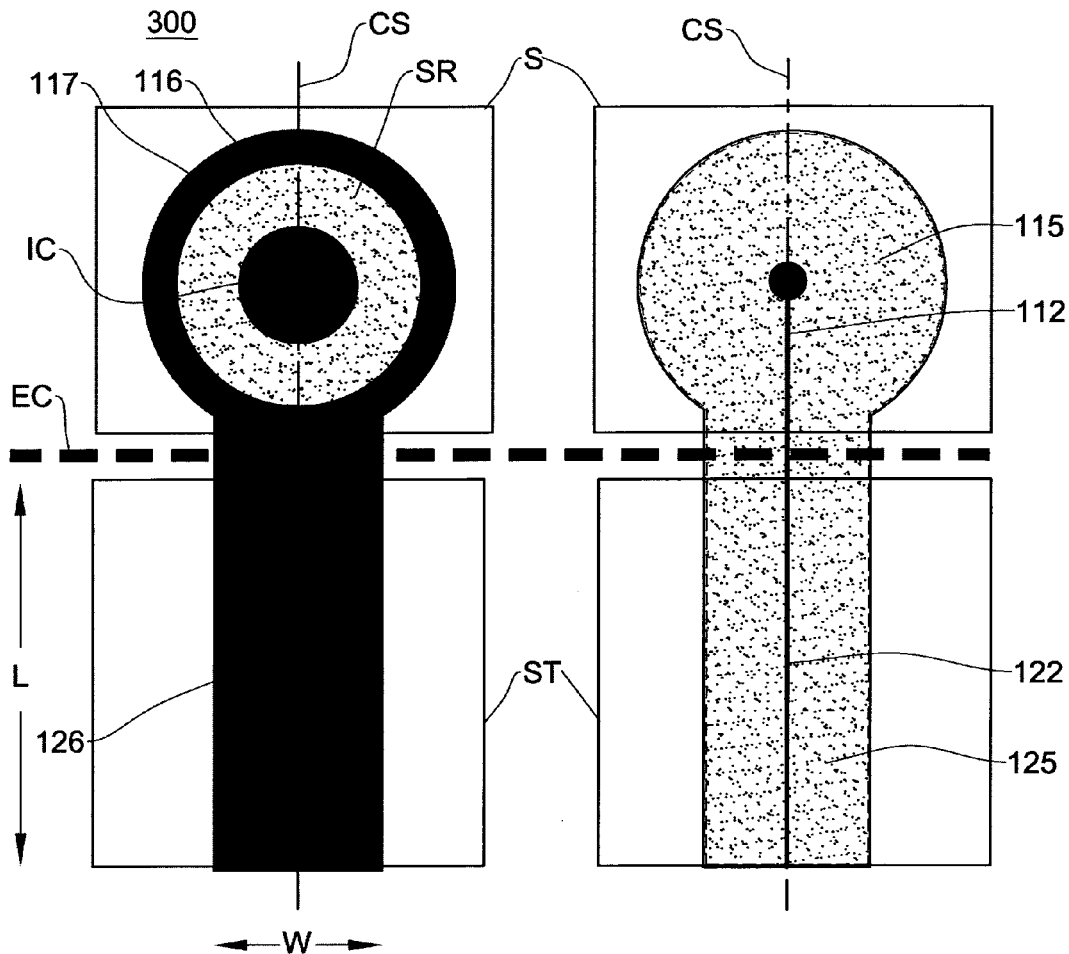
FIGS. 3A to 3C show different cross-sectional views of a tissue characterization assembly according to the present invention including an impedance controlled signal transmission structure integrated with a tissue characterization sensor.
Figure 3C:
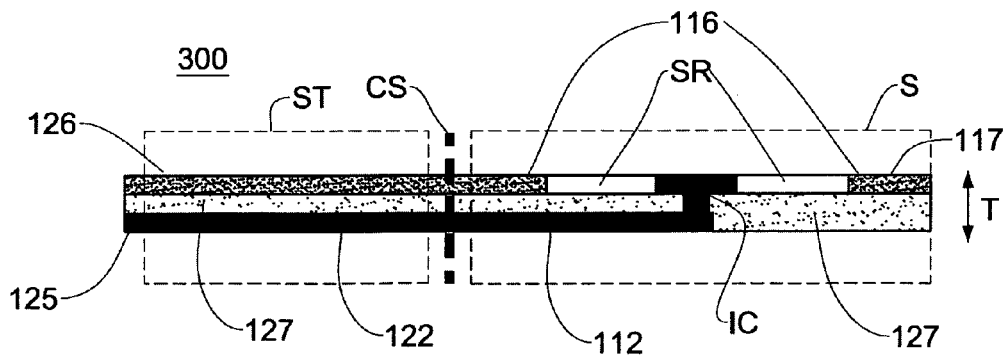

Reference is made to FIGS. 3A-3C illustrating more specifically different cross-action views of an example of a flat tissue characterization sensing assembly 300 according to an embodiment of the present invention which can be incorporated within an elongated and/narrow surgical tool. The tissue characterization sensing assembly 300 exemplified herein, includes tissue characterization sensor S and a flat and impedance controlled signal transmission structure ST electrically coupled together in a co-planar relationship. FIGS. 3A and 3B illustrate the front and back sides of the flat tissue characterization assembly 300; the sensing region SR of the sensor S is defined on the front side thereof. The cross section of the flat tissue characterization assembly 300 taken along the line CS of FIGS. 3A and 3B is illustrated in FIG. 3C. The width W, length L, and thickness T dimensions of the signal transmission structure ST are illustrated.

As shown, tissue characterization assembly 300 includes sensor S, defining a sensing surface/region SR, and signal transmission structure ST. Sensor S is configured as a near field EM sensor defining a sensing surface (coaxial aperture) SR surrounded by an electrically conductive material 116. The signal transmission structure ST is flexible and is integral with sensor S such that they have at least one common continuous surface (layer) 127. Signal transmission structure ST has a first layer 125 in which a signal connection line 122 is located being associated with the sensor S, e.g. being electrically connected/coupled to the sensor S (e.g. to an inner conductor element IC (element 118 in the sensor illustrated in FIG. 5A), to a signal line 112 thereof which is located on a first sensor layer 115 of the sensor S. Signal transmission structure ST has a second electrically conductive layer 126 electrically coupled to electrically conductive material 116 of the sensor S.

The sensor S is a multi-layer structure including at least a first sensor layer 115 (including said signal line 112) and a second conductive layer 117 including the electrically conductive material 116 and defining/enclosing the perimeter of the sensing region SR of the sensor S. Layers 115 and 117 are electrically isolated from each other (e.g. by using an electrically isolating laminate, adhesive, coating, or an additional isolation layer). In the present example, the electrical isolation is obtained by provision of an insulating (dielectric) layer 127 which serves as a substrate layer for both the layer 117 and the layer 115 of the sensor S and which is common also for the signal transmission structure ST. Accordingly, the first 125 and second 126 layers of the signal transmission structure ST are electrically isolated from one another by an the electric isolation layer 127.

Electric isolation layer 127 is formed as a common continuous surface of an integrated tissue characterization assembly 300. Additionally, the electrically conductive layer 126 signal transmission structure ST and the second conductive layer 117 of the sensor S are formed as common continuous surface of the integrated tissue characterization assembly 300.

It should be noted that in the present example, the signal transmission structure ST is configured with a single signal connection line 122 which is connected to one sensor S. However generally, a tissue characterization assembly, according to the present invention, may include a plurality of sensors electrically connected to the same signal transmission structure. In such cases, the signal transmission structure ST is typically configured with multiple signal connection lines 122 on the first layer 125 which are associated/electrically connected with the plurality of sensors. It should be noted that in cases where the tissue characterization assembly 300 includes a plurality of sensors that are arranged such that signal connection lines of at least one of the sensors traverses across (beneath) a sensing region of other sensor(s) it is preferable to include an additional conductive layer in between the second conductive layer and the first sensor layer of that other sensor(s) in order to screen (e.g. electro-magnetically mask) the sensing region of that sensor(s) from the signal transmitted through signal connection lines of the at least one of the sensors.

Figure 4A:
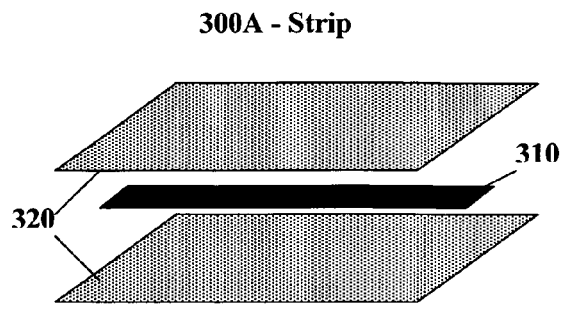
FIGS. 4A, 4B and 4C show examples of the impedance controlled signal transmission structure suitable to be used in the tissue characterization assembly of the present invention
Figure 4B:
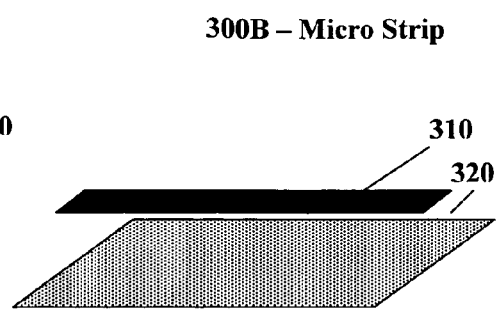
Figure 4C:
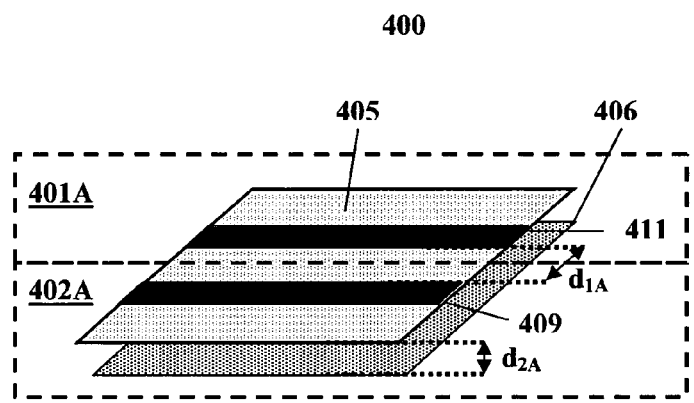

As noted above, the invention is not limited to any specific number of signal lines 122 in the signal transmission structure ST. Generally, as shown in FIGS. 4A-4C the signal transmission structure ST defines at least one signal connection line 122. However, the number of signal connection lines traversed through the signal transmission structure ST may vary in accordance with the desired numbers of sensors (S) on the surgical tool as well as in accordance with certain factors such as the required maximal width of signal transmission structure ST, the minimal signal to noise ratio (SNR) required. As the spacing between the signal connection lines 122 affects the cross talk between these lines 122 and reduces the SNR of the signal transmission, exceeding a certain number of signal connection lines 122 in the signal transmission structure ST, the width W of the signal transmission structure ST should be widened in order to maintain a desired level of SNR.

As also noted above, fitting one or more tissue characterization sensors to the distal region of a surgical tool enables to measure different properties in proximate regions of the tissue and in some configurations also mapping of certain characteristics of the tissue. It should be noted, however, that one of the prerequisites for such sensors is to provide signal transmission structure ST electrically coupled to the sensor(s) and adapted to enable readout of data (e.g. in the form of an EM signal) therefrom. Providing signal transmission structure ST with small dimensions that can be fitted in a small surgical may be especially cumbersome when the signal connection lines are required to propagate EM signals at high frequencies, for example above 1 Mhz. At such high frequencies, EM signals propagate as guided modes (or waves) along the signal connection lines 122 (which function, together with second electrically conductive layer 126, as wave guides) and accordingly such signals may suffer from various disturbances along their path impairing their accuracy. These disturbances may include, for example, absorbance and reflectance due to various factors of the signal lines such as a change of impedance (e.g. as a consequence of changes in material and/or geometrical dimensions along their propagation path) or interference and/or crosstalk with other signals (e.g. crosstalk between different signal transmission lines) due to, for example, lack of electrical screening of signal connection lines 122, or due to proximity of signal connection lines 122 to each other.

Accordingly, in order to maintain reliable and accurate signal transmission, signal transmission structure ST carrying the EM signals the sensor(s) is impedance controlled and optionally also electrically shielded. Generally, such signal transmission structures include at least one signal line which is located with a well defined, fixed, spatial relation to at least one electrically conductive surface associated therewith and arranged in its vicinity. The signal line and electrically conductive surface are interspaced by a dielectric, non-conductive, material spacer. The spatial relation between the signal line and the conductive surface, as well as the dimensions of the signal line and the material of the dielectric spacer, determine the impedance of the line.

Some examples of such impedance controlled structures, suited for use as signal transmission structures in the surgical tool of the present invention, are illustrated in FIGS. 4A, 4B, in which a strip planar feed structure 300A for signal transmission or signal communication, and a micro strip 300B planar feed structure are illustrated respectively. These structures comprise similar functional elements including a signal connection line 310 and one or more conductor surfaces 320 with a fixed spatial relation to the signal line. The signal line and the electrically conductive surface are interspaced by a dielectric, non-conductive, material spacer (not shown). Conductor surfaces 320 may also provide electrical-screening (shielding) to the EM signals propagating on signal line 310. Generally the strip structure 300A provides better electrical-shielding of the signal connection line 310 since it includes two conductor surfaces 320 located from both sides of the line 310. However, for the same reason, the strip structure is generally less flexible than the micro-strip structure 300B (the minimal bend radius below which the structure breaks (or yields, or reaches fatigue), and the minimal bend radius for which the structure can be elastically, or reversibly, deformed, are higher in the strip structure 300A). It should be noted that the conductor surface 320 may be integrated with one or more surfaces of the surgical tool. For example, such surface may serve as a ground plane/surface of the signal transmission structure.

According to the present invention, each sensor S (or each bunch thereof) may be associated with a dedicated signal connection line 122 of the signal transmission structure ST.

Line 122 is configured for propagating EM signals therethrough and thus to and from its corresponding sensor S. At the same time, allowing a static or dynamic bending of the signal transmission structure ST may be desired. This can be advantageous for example in order to enable flexibility of the signal transmission structure enabling a relative motion between different region/parts of the surgical tool and/or in-order to allow bending the signal transmission structure ST along curved facets of the surgical tool the allow tight fitting of the signal transmission structure thereto. For example, it might be specifically important when the surgical tool has a tubular shape (e.g. into or onto which the signal transmission structure ST should be fitted) or when back and forward movements of retractable/extractable parts of the surgical tool is sought on which a tissue characterization sensor is located.

Hence impedance controlled signal transmission structure and possibly also flexible structure is achieved in the present invention by utilizing a planar (i.e. flat) signal transmission structure. It should be understood that the terms "planar" and "flat" used for the purposes of the present application actually signify a relatively thin structure at least within a region thereof where the structure can thus be bent. Also, the sensor unit of the invention has a coplanar configuration in the meaning that the sensor part and the signal transmission part include at least one common continuous surface.

FIG. 4C illustrates schematically an example of signal transmission structure 400 according to some embodiments of the present invention. The signal transmission structure 400 is formed as a micro strip planar feed structure configuration and includes a first signal layer 405 that includes two spaced-apart signal lines 411 and 409, and a second conduction layer 406 that is electrically insulated from the first signal layer 405. The signal layer 405 and the second conduction layer 406 are interspaced by a dielectric, non-conductive, material spacer (not shown). Signal lines 411 and 409 and conduction layer 406 actually form a co-planar arrangement of two micro-strip feed structures 401A and 402A, in which a spacing $d_{1A}$ between the signal lines is to prevent cross-talk between signal lines 411 and 409. The spacing $d_{2A}$ between the conduction layer and signal layer, the type of dielectric spacers (not shown), and the width of the signal lines determine the impedance of the signal transmission structure. It should be understood that although in the example of FIG. 4C only two signal lines 411 and 409 are shown, one or more than two such signal lines can be arranged within each signal transmission band. It should be also understood that signal transmission structure 400 can be formed as a strip planar feed structure in which case it includes an additional conduction layer.

Thus, the type of signal transmission bands of the signal transmission structure is to be designed, inter alia, in accordance with the desired value of such parameters as the degree of allowable cross talk, the required width of the band and the number of signal lines that are to pass therethrough and the required band flexibility (e.g. the minimal possible bend radius of the transmission band that does not inflict structural damage to the band). Additionally, in some embodiments the flexibility of the signal transmission structure is required in order to allow for continuous and repetitive movement of the sensor relative to the probe housing.

Figure 5A:
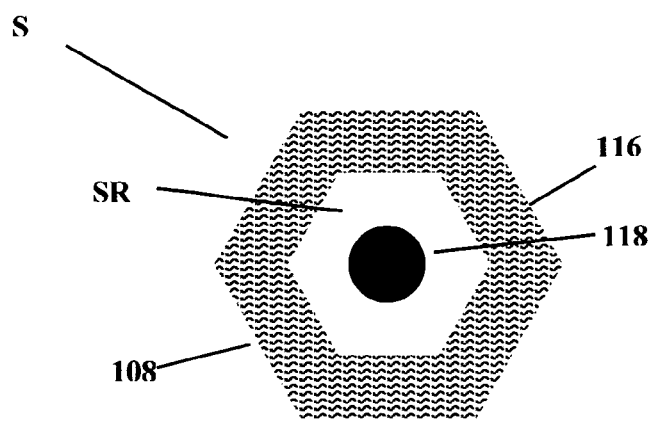
FIGS. 5A to 5F show examples of the configuration of tissue characterization sensors suitable for use in the present invention.
Figure 5B:
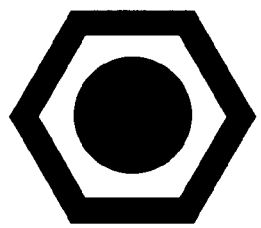
Figure 5C:
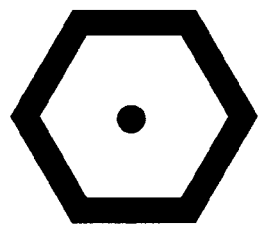

Reference is made to FIG. 5A showing the configuration of a near field EM sensor according to a specific but not limiting example. The figure shows a cross sectional view of the sensor S. Sensor S is configured as a Near field EM sensor cell S and defines a sensing region SR functioning as an aperture/opening or window with respect to the EM fields (region in which the EM fields induced by the sensor reside/exist), an inner conductor element 118 having distal and proximal ends (with respect to the inside of the sensor unit) accommodated such that the distal end is located within sensing region SR, and an electric conductive material 116 surrounding sensing region SR e.g. forming an electrically conductive contour/boundary at the perimeter of the sensor cell. It should be understood that generally a sensing region SR is not limited to a planar region but rather is typically a volumetric region. The distal end of inner conductor element 118 is located within the sensing region, while not necessarily in the sensing surface, e.g. being below the sensing surface. The distal portion of the inner conductor element is surrounded by the electrically conductive contour. It should be understood that inner conductor 118 is separated from electrically conductive contour 116 by dielectric material(s) of the sensor S within sensing region SR. As will be described further below, inner conductor element 118 by its opposite (proximal) end portion is electrically coupled to (e.g. physically connected with) a signal line (not shown here).

The inner conductor element 118 may be, for example, in the form of an electro-plated through-hole traversing across some layers of a multi-layer "flexible circuit" sensor. When sensor S is operated (i.e. when EM signals are transmitted to the sensor), it functions as a near field EM sensor inducing the near field EM fields within its sensing region SR, and thus in a tissue region located in the vicinity of sensing region SR. The type, extent and magnitude of the EM fields induced in said tissue region is dependent on the electrical characteristics of the tissue and on the frequency of the inducing signals. Hence, the analysis of the type and/or magnitude and/or phase of the EM signals induced in said tissue region provide data indicative of the characteristics of the tissue in the vicinity of the sensing region.

Figure 5D:
Figure 5E:
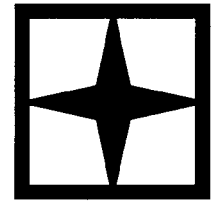
Figure 5F:
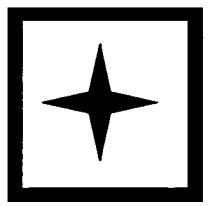

The contour of the sensor S may be of any suitable shape, e.g. hexagonal as shown in FIGS. 5A to 5D, as well as rectangular as shown in FIGS. 5E and 5F. Inner conductor element 118 of the sensors S may also be of any suitable cross sectional shape, e.g. circular (FIGS. 5A to 5C) or other shapes (FIGS. 5D to 5F).

In some embodiments of the invention, at least one sensor in the surgical tool is configured as a resistive type EM near field sensor. Each of such resistive type sensors includes the inner conductor element 118 electrically insulated from the surrounding electrically conductive material (contour) 116. This is shown in the examples of FIGS. 5A to 5C and 5F. The resistive type sensors may also include an electrical insulator material covering the sensing region so as to insulate the respective sensor cell from the subject. Alternatively, the resistive type sensor cell may be configured to perform measurements while both the inner conductor element 118 and the surrounding electrically conductive material 116 are in direct contact with the subject.

Alternatively or additionally, according to some other embodiments of the invention at least one sensor of the surgical tool is configured as inductive type sensors. Such sensors are illustrated for example in FIGS. 5D and 5E having their inner conductor element 118 connected to the electrically conductive material 116 surrounding the respective sensing region.

Figure 6:
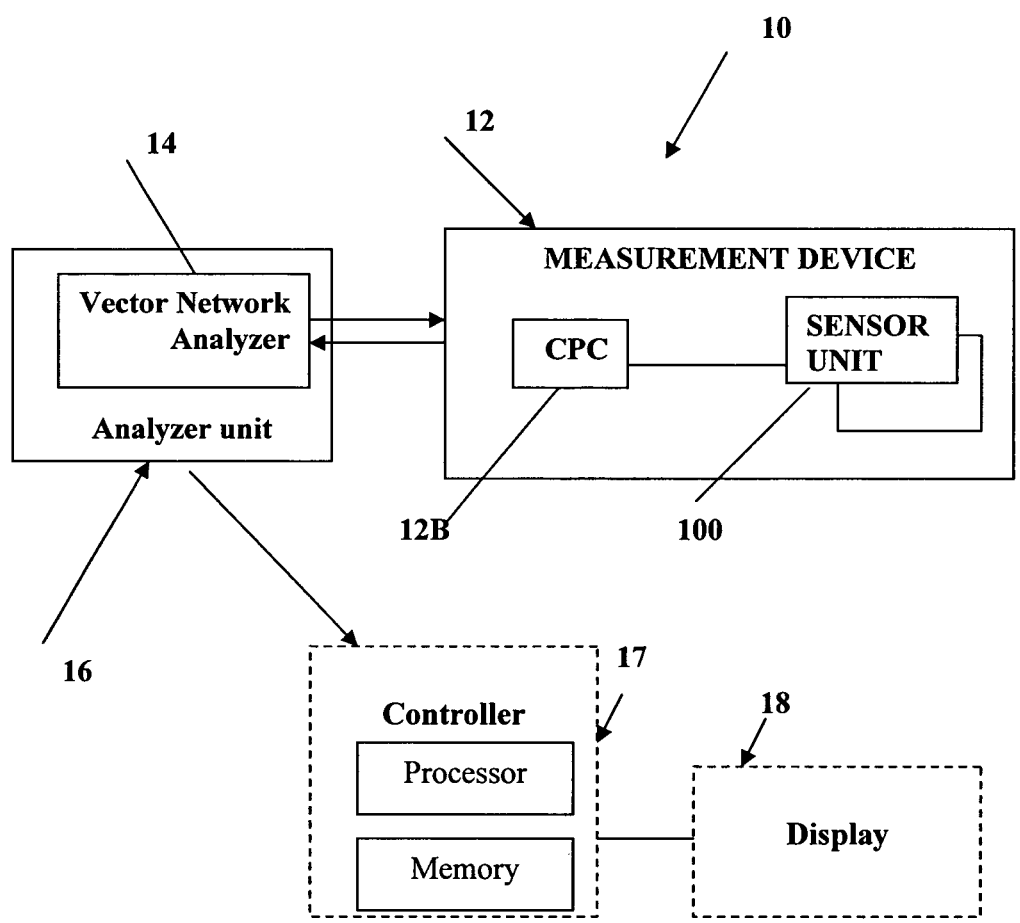
FIG. 6 is a block diagram of a measurement system comprising a measurement device utilizing surgical tool with tissue characterization assembly of the present invention with a calibration and probe control (CPC) unit.

It should be noted that the surgical tool equipped with the tissue characterization assembly can be associated with an appropriate calibration system, including a calibration unit connectable to a signal generation and reception unit e.g. network analyzer, for obtaining the type and/or magnitude and/or phase of the EM signals induced in the tissue regions located in the vicinity of the sensing regions SR of the sensors. This is schematically illustrated in FIG. 6, showing, by way of a block diagram, a measurement system, generally designated 10. The system 10 includes a measurement device 12 connectable to an analyzer 16. The measurement device 12 of the present invention includes one or more sensor units 100 and a calibration and probe control (CPC) unit 12B. The analyzer 16 includes a signal generation and reception unit 14, and also a suitable communication unit (not shown) for handling digital and/or analog communication with the CPC unit 12B.

The signal generation and reception unit 14 may be of any known suitable type and therefore need not be described in details, except to note that it is configured and operable for transmitting and receiving RF signals. Signal generation and reception unit 14 may be configured and operable as a vector network analyzer (VNA), for recording both the relative amplitude and the phase of RF signals. Signal generation and reception unit 14 is configured for carrying out the following: transmitting and receiving RF signals via its signal ports; analyzing the received signals to determine the amplitude and, optionally, phase thereof which are indicative of the signal interaction with calibration loads; and delivering the calibration correction parameters. Signal generation and reception unit 14 is also configured for measuring an RF response of the measurement device 12 using the calibration correction parameters. The analyzer 16 may have additional features, for example may be responsible for security issues to prevent reuse of the measurement device 12 or installation of other non-authorized measurement device in the system. Analyzer 16 may also provide at least one of the following facilities to measurement device 12: electrical power supply, means for handling digital and/or analog communication with measurement device 12, vacuum/pressure communication 19, a liquid dispensing line, optical signal communication, ultrasound signal communication, as well as provide control and power to an ablative/cutting apparatus/tool in measurement device 12, user and/or machine input and/or output, and control of other types of probes to be used in measurement device 12.

Figure 7A:
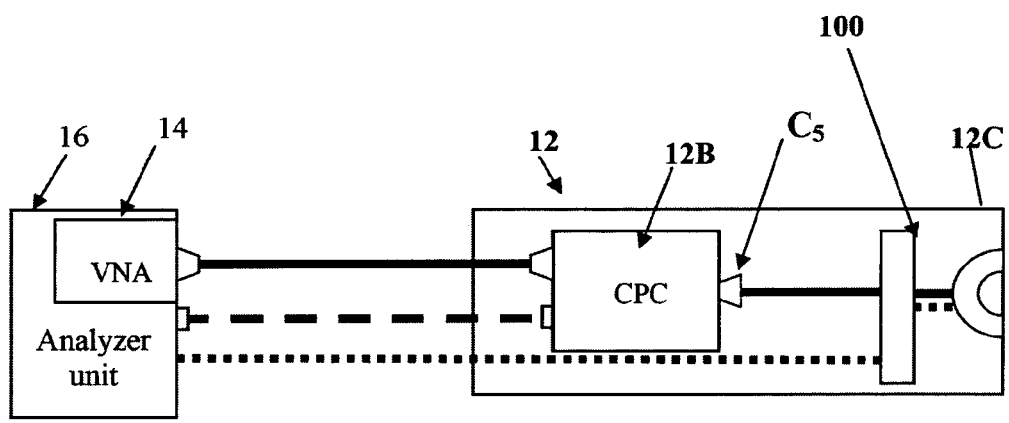
FIGS. 7A and 7B more specifically exemplify the configuration of the measurement device of FIG. 6.
Figure 7B:
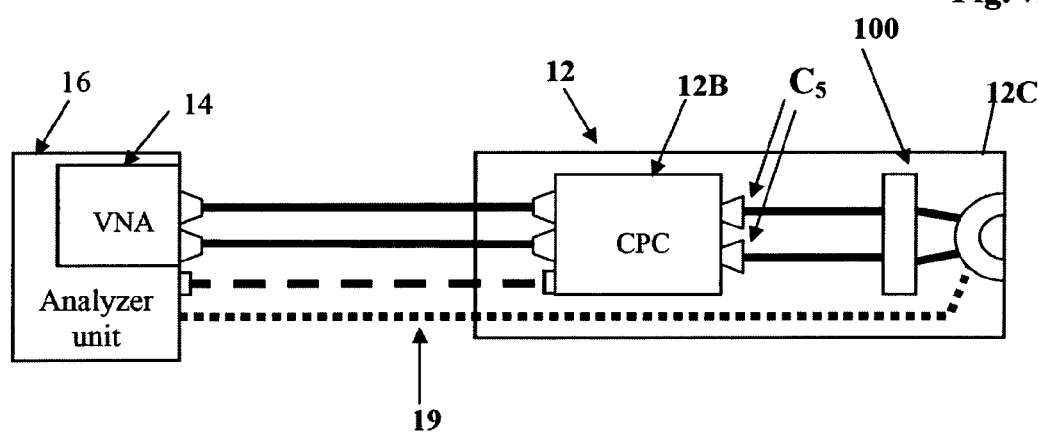

FIGS. 7A and 7B show specific but not limiting examples of the configuration of the measurement system 10. The measurement device 12 includes a sensor unit 100 and a CPC 12B integral with the sensor unit 100, which are accommodated in a common housing 12C. The sensor unit 100 is connected to the CPC 12B via a cable with an appropriate connector. In the example of FIG. 7A, there is only one RF signal connection (RF port connection) between the analyzer 16 and the measurement device 12. In the example of FIG. 7B, there are two RF signal connections (RF port connections) between the analyzer 16 and the measurement device 12. As shown in the figure, a vacuum/pressure communication line may be used for providing vacuum/pressure communication 19 to the sensor unit 100.

It should be appreciated that embodiments of the present invention may utilize more than two RF signal connections between analyzer 16 and measurement device 12. There may generally be n such RF signal connections (RF port connections) between the analyzer unit and measurement device, n being an integer equal to or greater than 1.

The CPC unit 12B is connected to the sensor unit 100 via an RF grade connector $C_5$. RF grade connector $C_5$ is generally connected to the signal transmission structure (e.g. ST1 of FIG. 1) of the tissue characterization assembly (e.g. TCA1 of FIG. 1) of the surgical tool of the invention (e.g. at the proximal end thereof). Accordingly RF grade connector $C_5$ is adapted for transferring therethrough one or more RF signals in between the sensors of the tissue characterization assembly and CPC unit. It should be understood that the RF grade connector $C_5$ may be associated with multiple RF channels (e.g. one for each sensor) and CPC unit may be operated for switching/directing the RF signal from the signal generation and reception unit 14 to the different RF channels associated with different sensors.

The CPC unit 12B includes a number of terminals associated with a plurality of calibration loads of known RF reflection coefficients respectively and includes a memory utility. The latter carries recorded data indicative of the RF reflection coefficients and recorded data indicative of RF transfer coefficients of the CPC unit. This configuration enables calculation of the RF response of each of the sensor cells within the sensing surface of the sensor unit, while remaining the sensor unit integral with CPC unit. It should be understood that the CPC may also be used for selectively directing EM signals to one or more sensor cells.

Preferably, the CPC unit 12B (implemented as a printed circuit board) is enclosed within a housing, having an RF cover, to provide mechanical strength and electromagnetic immunity to the CPC unit 12B. Mechanical strength of the housing enables better calibration by eliminating geometrical distortion, which may occur, for example, due to mechanical stresses or environmental changes of the CPC unit. This distortion may result in changes in the propagation of RF signals within the CPC unit, leading to degradation in calibration performance. Electromagnetic immunity of the housing enables better calibration by reducing RF interference of the CPC unit 12B with the sensor unit 100, and by reducing RF interference of external RF sources with the CPC unit 12B. Connectors of CPC unit 12B may be integrated into the housing. Housing may be constructed to enable operation of measurement device 12 in various environmental conditions, and to enable sterilization of the measurement device, by use of radiation and/or gas. The calibration unit 12B can generally have any suitable configuration, preferably either one of those disclosed in the co-pending International application PCT/IL2009/000611, assigned to the assignee of the present application, and which is incorporated herein by reference.

Turning back to FIG. 6, optionally according to some embodiments of the present invention, the surgical tool is associated with or may include a control unit 17 (controller) associated with display 18 (e.g. user interface system or graphical user interface (GUI). The controller 17 is connectable with the analyzer unit 16 and may be adapted for receiving and analyzing data indicative of the sensors' read outs and for presenting information corresponding to the readouts of the sensors (or corresponding to the predetermined conditions measured thereby) on the display 18. In the present example, the controller includes a processor and a memory module and is be adapted to process and optionally store information corresponding to the read outs from the sensors and also to allow post processing of that information (e.g. to determine statistical information there from).

Analysis/processing of the data indicative of the readouts from the sensors (e.g. data indicative of the predetermined conditions sensed thereby) by the controller 17 may include for example, spatial mapping of the predetermined conditions measured by the multiple sensors of the surgical tool. Accordingly these spatial mappings may be presented on the display 18 possibly together with the spatial relation between the locations of the sensors on the surgical tool.

Alternatively or additionally, the controller 17 may be adapted to process the data indicative of the readouts from the sensors and to determine statistical information corresponding to the distribution of the predetermined condition measured by the sensors. Such statistical data may include for example statistical parameters, such as the mean and standard deviation, of the spatial and/or temporal distributions of these predetermined conditions. The statistical information may be presented to the user through display 18 to thereby provide the user with supplementary information regarding the characteristics of the tissue in the vicinity of the distal region of the surgical tool.

Additionally or alternatively, the controller 17 may be also adapted for reconstructing the spatial registration of the readings from the sensors, as the tool is moved within the tissue/body based on comparison between successive readings from one or more sensors with known spatial relations between them. This also allows scanning of the tissue during the movement of the surgical tool therein.

It should be also noted that optionally, one or more position sensors and/or state position sensors (not shown) may also be incorporated within the surgical tool. The position sensors may be configured to provide indication of the position of the surgical tool with respect to the inspected substance/tissue (e.g. such sensors may be located on a fixture of the tool). The state position sensors may be configured for providing indication to the relative positions of different movable components/parts of the surgical tool (e.g. relative position between the inner and outer cannulas of biopsy needle). Accordingly the controller 17 may utilize readouts from these position and state position sensors to determine the location of the surgical tool and/or its sub-components within the tissue. Moreover, such locations can be further used and synchronized with the predetermined conditions measured by the tissue characterization sensors to provide spatial reconstruction of the readings from the tissue characterization sensors.

Optionally, when the tissue characterization sensors are located at different location from the tissue sampling port (e.g. recess RS in FIG. 1), output from position and state position sensors may be used to spatially synchronize between the readouts from tissue characterization sensor(s) and tissue collection/sampling. For example, when the sensor(s) S11 of FIG. 2A provide a reading that requires, or calls for tissue sampling, the output from the position sensor may be used in order to indicate how much should the surgical tool be advanced/extracted in order for the tissue that was indicated for sampling will be within the region of the tissue sampling port 426.

Those skilled in the art will readily appreciate that various modifications and changes can be applied to the embodiments of the invention as hereinbefore described without departing from its scope defined in and by the appended claims.

The invention claimed is:

1. A surgical tool for use in a tissue removal procedure from a subject, the surgical tool comprising:
    an elongated body comprising proximal and distal regions; and
    one or more flat tissue characterization assemblies, wherein each of said one or more flat tissue characterization assemblies comprises:
        a flat sensor unit located at the distal region of said elongated body, comprising a sensing surface by which the flat sensor unit faces a region of interest, and one or more flat sensors each being configured for sensing one or more predetermined conditions, and each comprising a sensing region located in said sensing surface; and a single flat and thin signal transmission structure, extending between the proximal region of said elongated body and said sensing surface of said flat sensor unit and being electrically connected with said flat sensor unit, said single flat and thin signal transmission structure comprising one or more signal connection lines each associated with a respective one of said one or more flat sensors, wherein said single flat and thin signal transmission structure and said flat sensor unit are integrally coupled in a co-planar configuration forming a flat and thin integral structure, such that said single flat and thin signal transmission structure and said flat sensor unit have in common at least one continuous surface that is parallel, at the distal region of said elongated body, to the sensing surface of said flat sensor unit, said flat and thin integral structure thereby enabling impedance controlled signal transmission between said sensing surface of said flat sensor unit and said proximal region of said elongated body.

2. The surgical tool of claim 1, being configured and operable as a biopsy tool.

3. The surgical tool of claim 2. being configured and operable as a biopsy needle.

4. The surgical tool of claim 2, wherein said single flat and thin signal transmission structure is a flexible structure.

5. The surgical tool of claim 1, wherein said elongated body comprises a cavity for collection of a tissue being removed.

6. The surgical tool of claim 5, wherein said single flat and thin signal transmission structure is a flexible structure.

7. The surgical tool of claim 1, wherein said one or more flat sensors are configured and operable as tissue characterization sensors.

8. The surgical tool of claim 7, wherein said one or more flat tissue characterization sensors are near field electromagnetic sensors, at least one of the near field electromagnetic sensors comprising a coaxial sensing aperture surrounded by an electrically conductive material, such that when the tool is in operation the at least one of the near field electromagnetic sensors is configured to face a tissue portion by said coaxial sensing aperture.

9. The surgical tool of claim 1, wherein each of said one or more flat sensors comprises a coaxial sensing aperture.

10. The surgical tool of claim 1, wherein said single flat and thin signal transmission structure further comprises an electrically conductive layer.

11. The surgical tool of claim 10, wherein said one or more flat sensors comprise at least one near field electromagnetic sensor comprising a coaxial sensing aperture surrounded by an electrically conductive material, such that when the tool is in operation the at least one near field electromagnetic sensor is configured to face a tissue portion by said coaxial sensing aperture.

12. The surgical tool of claim 1, wherein said one or more flat sensors comprise at least one near field electromagnetic sensor comprising a coaxial sensing aperture surrounded by an electrically conductive material, such that when the tool is in operation the at least one near field electromagnetic sensor is configured to face a tissue portion by said coaxial sensing aperture.

13. The surgical tool of claim 12, wherein said at least one near field electromagnetic sensor comprises an inner conductor element coupled to inside of said coaxial sensing aperture and electrically coupled to one of said one or more signal connection lines of said single flat and thin signal transmission structure.

14. The surgical tool of claim 13, wherein said at least one near field electromagnetic sensor is configured as a resistive type sensor, the inner conductor element thereof being electrically insulated from the surrounding electrically conductive material.

15. The surgical tool of claim 14, wherein said at least one near field electromagnetic sensor comprises an electrical insulator material covering the coaxial sensing aperture and adapted for insulating said at least one near field electromagnetic sensor from a tissue.

16. The surgical tool of claim 13, wherein said at least one near field electromagnetic sensor is configured to perform measurement while the inner conductor element and the surrounding electrically conductive material are brought in direct contact with a tissue.

17. The surgical tool of claim 16, wherein said at least one near field electromagnetic sensor is configured as an inductive type sensor, the inner conductor element thereof being electrically connected to the surrounding electrically conductive material.

18. The surgical tool of claim 12, wherein said single flat and thin signal transmission structure is a flexible structure.

19. The surgical tool of claim 1, wherein said single flat and thin signal transmission structure is a flexible structure.

20. The surgical tool of claim 19, wherein at least a part of said flexible structure is configured for engaging with a curved facet of said surgical tool located in between said distal and proximal regions of said elongated body.

21. The surgical tool of claim 20, comprising an extendible part which is shiftable between retracted and extracted positions with respect to the proximal region of said elongated body, said extendible part having at least one flat sensor, of said one or more flat sensors, accommodated thereon, said flexible structure being electrically connected to said at least one flat sensor accommodated on said extendible part, and being configured to allow extraction and retraction of said extendible part in between said positions.

22. The surgical tool of claim 19, comprising an extendible part which is shiftable between retracted and extracted positions with respect to the proximal region of said elongated body, said extendible part having at least one flat sensor, of said one or more flat sensors, accommodated thereon, said flexible structure being electrically connected to said at least one flat sensor accommodated on said extendible part, and being configured to allow extraction and retraction of said extendible part in between said positions.

23. The surgical tool of claim 1, wherein said one or more flat sensors comprises at least two flat sensors located on the distal region of said elongated body.

24. The surgical tool of claim 23, wherein said at least two flat sensors are arranged within said distal region of said elongated body in a spaced apart relationship along a direction between said proximal and distal regions of said elongated body.

25. The surgical tool of claim 1, wherein said at least one continuous surface is constituted by a layer.

* * * * *